United States Patent
Franklin et al.

(10) Patent No.: US 10,417,357 B2
(45) Date of Patent: Sep. 17, 2019

(54) PATIENT AND PROCEDURE CUSTOMIZED FIXATION AND TARGETING DEVICES FOR STEREOTACTIC FRAMES

(71) Applicant: Neutar, LLC, Bowdoinham, ME (US)

(72) Inventors: Ronald J. Franklin, Bowdoin, ME (US); Joel I. Franck, Panama City Beach, FL (US); Frederick C. Haer, Brunswick, ME (US)

(73) Assignee: Neutar, LLC, Bowdoinham, ME (US)

( * ) Notice: Subject to any disclaimer, the term of this patent is extended or adjusted under 35 U.S.C. 154(b) by 356 days.

(21) Appl. No.: 15/223,127

(22) Filed: Jul. 29, 2016

(65) Prior Publication Data

US 2016/0335380 A1    Nov. 17, 2016

Related U.S. Application Data

(63) Continuation of application No. 14/382,935, filed as application No. PCT/US2013/029827 on Mar. 8, 2013, now abandoned.
(Continued)

(51) Int. Cl.
*A61B 19/00* (2006.01)
*G06F 17/50* (2006.01)
(Continued)

(52) U.S. Cl.
CPC .......... *G06F 17/5009* (2013.01); *A61B 34/10* (2016.02); *A61B 34/20* (2016.02);
(Continued)

(58) Field of Classification Search
CPC ..... G06F 17/5009; A61B 34/10; A61B 34/20; A61B 90/10; A61B 90/14; A61B 90/39;
(Continued)

(56) References Cited

U.S. PATENT DOCUMENTS 2,697,433 A    12/1954  Zehnder
3,135,263 A     6/1964  Connelley, Jr.
(Continued)

FOREIGN PATENT DOCUMENTS

WO          9513578 A1    5/1995
WO       2006033064 A2    3/2006

OTHER PUBLICATIONS

Grunert, "Accuracy of stereotactic coordinate transformation using a localization frame and computed tomographic imaging. Part II. Analysis of matrix-based coordinate transformation", Neurosurg. Rev., 1999, pp. 188-203, vol. 22.
(Continued)

*Primary Examiner* — Mallika D Fairchild
(74) *Attorney, Agent, or Firm* — The Webb Law Firm

(57) ABSTRACT

Provided herein are methods and apparatuses for performing precise medical procedures. Provided are methods of providing unitary positioning interfaces for stereotactic devices or medical devices. The methods include implanting emitters in a patient, scanning the patient using any suitable scanning technique, determining orientation and location data of the emitters and any suitable anatomic structures, generating a digital image, and fabricating a solid physical model from the digital image. Also provided herein are methods of verifying medical treatments and systems for performing medical procedures.

13 Claims, 9 Drawing Sheets

Related U.S. Application Data

(60) Provisional application No. 61/608,200, filed on Mar. 8, 2012.

(51) Int. Cl.
*A61B 34/20* (2016.01)
*A61B 90/14* (2016.01)
*A61B 34/10* (2016.01)
*A61B 90/00* (2016.01)
*A61B 90/10* (2016.01)
*A61N 5/10* (2006.01)

(52) U.S. Cl.
CPC .............. *A61B 90/10* (2016.02); *A61B 90/14* (2016.02); *A61B 90/39* (2016.02); *A61N 5/1039* (2013.01); *A61B 2034/102* (2016.02); *A61B 2034/104* (2016.02); *A61B 2034/107* (2016.02); *A61B 2034/108* (2016.02); *A61B 2034/2051* (2016.02); *A61B 2034/2063* (2016.02); *A61B 2034/2065* (2016.02); *A61B 2090/0812* (2016.02); *A61B 2090/101* (2016.02); *A61B 2090/363* (2016.02); *A61B 2090/374* (2016.02); *A61B 2090/3762* (2016.02); *A61B 2090/3975* (2016.02); *A61B 2090/3983* (2016.02); *Y10T 29/49826* (2015.01)

(58) Field of Classification Search
CPC ........ A61B 2034/104; A61B 2034/107; A61B 2090/101; A61N 5/1039
See application file for complete search history.

(56) References Cited

U.S. PATENT DOCUMENTS

| | | |
|---|---|---|
| 3,777,124 A | 12/1973 | Pavkovich |
| 4,222,104 A | 9/1980 | Moore |
| 4,256,112 A | 3/1981 | Kopf et al. |
| 4,262,306 A | 4/1981 | Renner |
| 4,341,220 A | 7/1982 | Perry |
| 4,350,159 A | 9/1982 | Gouda |
| 4,463,758 A | 8/1984 | Patil et al. |
| 4,583,538 A | 4/1986 | Onik et al. |
| 4,592,352 A | 6/1986 | Patil |
| 4,608,977 A | 9/1986 | Brown |
| 4,617,925 A | 10/1986 | Laitinen |
| 4,618,978 A | 10/1986 | Cosman |
| 4,638,798 A | 1/1987 | Shelden et al. |
| 4,651,335 A | 3/1987 | Kalender et al. |
| 4,706,665 A | 11/1987 | Gouda |
| 4,791,934 A | 12/1988 | Brunnett |
| 4,805,615 A | 2/1989 | Carol |
| 4,838,265 A | 6/1989 | Cosman et al. |
| 4,841,967 A | 6/1989 | Chang et al. |
| 4,869,247 A | 9/1989 | Howard, III et al. |
| 4,896,673 A | 1/1990 | Rose et al. |
| 4,955,891 A | 9/1990 | Carol |
| 5,027,818 A | 7/1991 | Bova et al. |
| 5,047,036 A | 9/1991 | Koutrouvelis |
| 5,050,608 A | 9/1991 | Watanabe et al. |
| 5,056,523 A | 10/1991 | Hotchkiss, Jr. et al. |
| 5,078,140 A | 1/1992 | Kwoh |
| 5,080,662 A | 1/1992 | Paul |
| 5,107,839 A | 4/1992 | Houdek et al. |
| 5,116,345 A | 5/1992 | Jewell et al. |
| 5,117,829 A | 6/1992 | Miller et al. |
| 5,129,911 A | 7/1992 | Siczek et al. |
| 5,142,559 A | 8/1992 | Wielopolski et al. |
| 5,163,430 A | 11/1992 | Carol |
| 5,165,410 A | 11/1992 | Warne et al. |
| 5,178,146 A | 1/1993 | Giese |
| 5,186,174 A | 2/1993 | Schlondorff et al. |
| 5,197,476 A | 3/1993 | Nowacki et al. |
| 5,207,223 A | 5/1993 | Adler |
| 5,211,164 A | 5/1993 | Allen |
| 5,221,283 A | 6/1993 | Chang |
| 5,222,499 A | 6/1993 | Allen et al. |
| 5,230,623 A | 7/1993 | Guthrie et al. |
| 5,242,455 A | 9/1993 | Skeens et al. |
| 5,247,555 A | 9/1993 | Moore et al. |
| 5,257,998 A | 11/1993 | Ota et al. |
| 5,263,956 A | 11/1993 | Nobles |
| 5,269,305 A | 12/1993 | Corol |
| 5,281,232 A | 1/1994 | Hamilton et al. |
| 5,285,772 A | 2/1994 | Rattner |
| 5,285,787 A | 2/1994 | MacHida |
| 5,295,483 A | 3/1994 | Nowacki et al. |
| 5,298,115 A | 3/1994 | Leonard |
| 5,299,254 A | 3/1994 | Dancer et al. |
| 5,300,076 A | 4/1994 | Leriche |
| 5,300,080 A | 4/1994 | Clayman et al. |
| 5,309,913 A | 5/1994 | Kormos et al. |
| 5,315,630 A | 5/1994 | Sturm et al. |
| 5,329,567 A | 7/1994 | Ikebe |
| 5,354,314 A | 10/1994 | Hardy et al. |
| 5,365,996 A | 11/1994 | Crook |
| 5,370,692 A | 12/1994 | Fink et al. |
| 5,383,454 A | 1/1995 | Bucholz |
| 5,387,220 A | 2/1995 | Pisharodi |
| 5,389,101 A | 2/1995 | Heilbrun et al. |
| 5,397,329 A | 3/1995 | Allen |
| 5,398,684 A | 3/1995 | Hardy |
| 5,423,832 A | 6/1995 | Gildenberg |
| 5,446,548 A | 8/1995 | Gerig et al. |
| 5,464,411 A | 11/1995 | Schulte et al. |
| 5,531,229 A | 7/1996 | Dean et al. |
| 5,588,430 A | 12/1996 | Bova et al. |
| 5,595,703 A | 1/1997 | Swaelens et al. |
| 5,622,170 A | 4/1997 | Schulz |
| 5,627,949 A | 5/1997 | Letcher, Jr. |
| 5,638,819 A | 6/1997 | Manwaring et al. |
| 5,662,111 A | 9/1997 | Cosman |
| 5,682,890 A | 11/1997 | Kormos et al. |
| 5,702,406 A | 12/1997 | Vilsmeier et al. |
| 5,715,836 A | 2/1998 | Kliegis et al. |
| 5,728,106 A | 3/1998 | Misko et al. |
| 5,732,703 A | 3/1998 | Kalfas et al. |
| 5,741,215 A | 4/1998 | D'Urso |
| 5,752,962 A | 5/1998 | D'Urso |
| 5,768,134 A | 6/1998 | Swaelens et al. |
| 5,776,064 A | 7/1998 | Kalfas et al. |
| 5,776,143 A | 7/1998 | Adams |
| 5,792,146 A | 8/1998 | Cosman |
| 5,792,147 A | 8/1998 | Evans et al. |
| 5,807,252 A | 9/1998 | Hassfeld et al. |
| 5,823,778 A | 10/1998 | Schmitt et al. |
| 5,836,954 A | 11/1998 | Heilbrun et al. |
| 5,848,967 A | 12/1998 | Cosman |
| 5,855,582 A | 1/1999 | Gildenberg |
| 5,891,157 A | 4/1999 | Day et al. |
| 5,891,158 A | 4/1999 | Manwaring et al. |
| 5,961,454 A | 10/1999 | Kooy et al. |
| 5,967,982 A | 10/1999 | Barnett |
| 5,971,997 A | 10/1999 | Guthrie et al. |
| 5,978,349 A | 11/1999 | Yoshinari et al. |
| 5,978,696 A | 11/1999 | VomLehn et al. |
| 5,980,535 A | 11/1999 | Barnett et al. |
| 6,006,126 A | 12/1999 | Cosman |
| 6,011,987 A | 1/2000 | Barnett |
| 6,026,315 A | 2/2000 | Lenz et al. |
| 6,167,292 A | 12/2000 | Badano et al. |
| 6,236,875 B1 | 5/2001 | Bucholz et al. |
| 6,240,308 B1 | 5/2001 | Hardy et al. |
| 6,246,898 B1 | 6/2001 | Vesely et al. |
| 6,259,943 B1 | 7/2001 | Cosman et al. |
| 6,273,896 B1 | 8/2001 | Franck et al. |
| 6,275,723 B1 | 8/2001 | Ferris et al. |
| 6,282,437 B1 | 8/2001 | Franck et al. |
| 6,738,657 B1 | 5/2004 | Franklin et al. |
| 7,657,301 B2 | 2/2010 | Mate et al. |
| 8,721,660 B2 | 5/2014 | Ulfarsson et al. |
| 2003/0120143 A1 | 6/2003 | Franklin et al. |

(56) References Cited

U.S. PATENT DOCUMENTS

2003/0187351 A1   10/2003   Franck et al.
2005/0055035 A1    3/2005   Cosman, Jr. et al.
2011/0098722 A1    4/2011   Ulfarsson et al.
2013/0172898 A1    7/2013   Iannotti et al.

OTHER PUBLICATIONS

Leksell Gamma Knife 4C—System Description, 2004, Elekta AB, Sweden.
Leksell Gamma Knife 4C—Refining the Art of Radiosurgery, 2004, Elekta AB, Sweden.
Leksell Multi Purpose Stereotactic Arc—Instructions for Use, 2004, Elekta AB, Sweden.
Plastic laser sintering system FORMIGA P 110 for the direct manufacture of series, spare parts and functional prototypes, EOS, 2006, Germany.
http://www.integralife.com/Neurosurgeon/Neurosurgeon-Product-Detail.aspx?Product=35, Relocatable Head Rings—Solutions, printed from the Internet Jul. 26, 2011.

though the alignment is never perfect.
PATIENT AND PROCEDURE CUSTOMIZED FIXATION AND TARGETING DEVICES FOR STEREOTACTIC FRAMES This application is a continuation of U.S. patent application Ser. No. 14/382,935, filed Sep. 4, 2014, which is the United States national phase of International Application No. PCT/US2013/029827, filed Mar. 8, 2013, which claims priority to U.S. Provisional Patent Application No. 61/608,200, filed Mar. 8, 2012, the disclosures of which are hereby incorporated in their entirety by reference.

BACKGROUND OF THE INVENTION

Field of the Invention

This invention relates to equipment and methods for performing surgery, more specifically the invention relates to a customized fixation and targeting system for stereotactic frames.

Description of Related Art

In many medical procedures, it is of utmost necessity that the patient be stabilized in a fixed, unmoving position. This is particularly true of surgery that occurs in the region of the head, neck, and spinal cord. The precise measurements and movements that are involved with surgery of this type demand that the patient be immobilized so that a surgeon's movements can be carefully calibrated to a known safe trajectory through critical regions of, for example, the cerebral cortex or the spinal column.

An additional consideration for these surgeries, as alluded to above, is that a safe, known trajectory must exist in the situations where a surgeon must reach deep tissue, for example, the subthalamic nucleus (STN). Given the location of this brain structure, a surgeon must plan a careful route for accessing the region that will not compromise other areas of the brain that lie between the skull and the deep brain, such as motor and sensory regions.

As the need for precise surgeries has become more prevalent, novel means of planning a safe route to deep tissue and of ensuring that the route remains static during surgery have been developed. One of the most common is the stereotactic frame, which has been in use in one form or another since the 1940s. For example, U.S. Pat. No. 4,341,220 discloses a frame fixed to a patient's head and defining a three-dimensional coordinate system in which a surgical device may be precisely positioned. A frame such as disclosed therein may also have markers detectable via X-ray, so that when the frame is attached to the patient's skull, markers on the frame are visible on a scan, for example a computed tomography (CT) scan, along with the brain structure of interest.

The process of scanning a patient with a stereotactic frame containing visible markers is referred to as registering the frame to the patient. The way this registration is accomplished is to scan the patient with the stereotactic device attached. The device then acts as a known reference point in relation to the patient's anatomy. A surgeon may then visualize a route to the target by utilizing the coordinates of the markers and of the brain structure, allowing for a pre-planned route that avoids other critical areas. In this way, the stereotactic frame can be manipulated by the surgeon to provide a customized path to the target structure. These procedures, however, are not without substantial drawbacks.

One common modern device for these surgeries is a frame such as disclosed in U.S. Pat. No. 5,423,832, which includes a head ring attached to the patient by four fixation posts holding pins that screw in to contact the skull. These pins, such as those disclosed in U.S. Pat. No. 5,300,076, must be secure enough to hold the weight of the stereotactic frame and in some cases the weight of the patient's head in a prone position without slipping. To do this, the pins must penetrate skin and bone, creating a divot in the skull. This can be a painful and disturbing process for the patient. Using the adjustments available in the fixation posts and the pins, the surgeon attempts to align the head ring with known but not visible anatomical points in the brain that will be visible in the scan, and with planes that coincide with anatomical atlases used to navigate the brain. This is difficult under the circumstances, and the alignment is never perfect.

In a typical modern cranial surgical procedure, after the ring is attached, a fiducial box with radiopaque markers or bars of known geometry is fixed to the ring. Once the patient has been scanned with the head ring and fiducial box attached, the images are loaded into a computerized surgical planning computer. Here the fiducial markers are plotted and the location and orientation of the stereotactic frame coordinate system (FCS) based on the head ring is determined in relation to the patient's anatomy in the images. A surgical target is located in the patient images, and an entry point on the skull is determined. Based on these locations, frame adjustment settings are determined that will provide a trajectory from the frame instrument mounting location to the target through the selected entry point. These calculated settings correct for the misalignment of the frame to the patient's anatomical reference system (PRS) and then find an adjustment setting that puts the frame's FCS center at the selected target. This surgical planning may take some time, since the surgeon must determine a trajectory that avoids blood vessels and areas that could be damaged by instrument penetration, causing complications, injury, or death.

While this surgical path is planned, the patient is in an awake condition, often experiencing discomfort and anxiety. The ring cannot be removed without losing the registration that has been achieved through the previous scanning. The operating room is prepared for the surgery, but since the planning has to be done after the patient is scanned, and the period of time required varies, it is difficult to schedule the surgical procedure exactly, leading to wasted valuable operating room time. After the planning is done the patient is taken to the operating room, and the adjustable parts of the stereotactic frame are set to the calculated settings to reach the target and then attached to the head ring.

Some stereotactic frame systems have what is called a "phantom", which is used before attaching the frame to the patient to verify the correct settings of the frame. The identical settings are dialed into the phantom and its duplicate head ring. The upper frame portion is then attached to the duplicate head ring and a probe is used in the adjustable frame portion to determine that it places the probe tip at the correct target center. The phantom does not verify targeting, since it has no reference to patient anatomy. It verifies only that the frame is set correctly to the calculated figures.

In addition to providing precise paths through brain tissue, head rings and stereotactic frames described above can also be used for securing a patient during sensitive irradiation procedures. The above-described method of registering is similar. However, rather than attach a stereotactic frame with an adjustable guide for surgical procedures, the ring itself is connected to an irradiation device, immobilizing the patient in a position calculated based on the known relationship between the head ring and the patient's brain structures so a concentrated focal point of radiation targets, for example, a tumor or lesion, is in a known position relative to the trajectory of irradiation beams. One example of such a device is the Elekta Gamma Knife®. Practically, however, this current method limits the patient to one or a very few number of procedures, since repeated treatments require a reapplication of the head ring, rescanning, and re-planning.

In newer versions of such devices, the travel and size of the treatment area have been increased to allow the radiosurgical treatment of tumors and lesions in the neck and cervical spine. The use of this new device for such treatment has been limited due to the difficulty of fixating the head and neck in relation to the upper body of the patient. Since the neck is capable of a great range of motion, the use of the current head ring mounting system of the standard stereotactic frame does not sufficiently restrain the patient's neck and cervical spine enough to allow safe and accurate targeting of neck and upper spine lesions.

The drawbacks to the existing technology are numerous. Current head rings rely on fixation posts that penetrate skin and bone and exert pressure on the skull of a patient, resulting in a painful and anxious experience. Initial placement and alignment of the ring is difficult due to the surgeon's inability to see the underlying brain structures, and the relation of the ring to those structures, until after the initial scan. Once the ring is attached, it cannot be removed, for example in a situation where multiple surgeries or treatments are required, without the need to re-register the ring to the patient, followed by time-consuming re-planning of the surgical or treatment route. Once the frame is attached to the ring, alignment is often inconsistent with the PRS and relies on an algorithm to correct any misalignment. Additionally, as new techniques become available for procedures on the neck and spine, the current frame technology is incapable of safely securing patients for precise treatment of those areas.

Accordingly, there is a need in the art for a fixation and targeting system that is less invasive for the patient, but that provides a high level of precision and accuracy for the surgeon engaged in procedures of the head, neck, and spine.

SUMMARY OF THE INVENTION

The present invention provides a method of providing a unitary positioning interface for a stereotactic frame system. The method is conducted by implanting a plurality of anchors in a patient's body, scanning the patient's body and thus providing a three-dimensional scanned image of the body. The image will contain at least a portion of the implanted anchors and at least one anatomical point within the body. The method further includes determining, from the at least one image, location and orientation data relating to at least a portion of the anchors and the at least one anatomical point. At least a portion of this data is then inputted into a computer system, where a patient reference map is produced. A pre-determined stereotactic frame coordinate map is then positioned in a manner such that the frame coordinate map is aligned with the at least one anatomical point, and the frame coordinate map is then rotated about that anatomical point to coincide with the patient reference map. From the data, a digital model is then produced, the digital model containing a plurality of positioning interface devices, the patient reference system, the frame coordinate system, and the location and orientation of at least a portion of the plurality of anchors and the at least one anatomical point. In a subsequent step, a plurality of positioning interface devices are fabricated from the digital model.

In some embodiments, the anchors are detectable emitters, which may be passive or active. Further, the three-dimensional scanned image may be obtained through a CT scan, a T1-weighted or T2-weighted magnetic resonance imaging (MRI) scan, or a positron emission topography (PET) scan.

In some embodiments, the anatomical point of the scanned image is a brain structure. In non-limiting embodiments, the brain structure is the anterior commissure (AC), posterior commissure (PC), and/or the mid-commissural point (MCP). In a further embodiment, the patient reference map originates at the MCP.

The digital model formed from the data of the scanned image may also contain stereotactic head ring mounts for the positioning interface devices as well as a stereotactic targeting device or fiducial registration device. Additionally, the digital model may also contain at least one surgical entry point.

The three-dimensional scanned image may also contain at least one target point within the body. In this way, the orientation and location data, and the digital model, will each contain the at least one target. When target data is included, a further step in the method may include calculating, from the frame reference map, patient reference map, and the location and orientation data of the at least one anatomical point, at least one target, and at least a portion of the anchors, stereotactic frame settings for a medical procedure. The medical procedure in this embodiment may be directed at the at least one target.

In addition to fabricating a plurality of positioning interface devices, the fabricating step may also include fabricating a solid physical model of the target. In this way, the surgical procedure may be simulated with precision due to the specific positioning interface devices and the target drawn specifically to the area of interest of the patient. The fabricating may be by high-speed laser sintering or traditional machining. High-speed machining may also be utilized. In certain embodiments, the positioning interface devices are fixation posts for a stereotactic frame.

Also provided herein are positioning devices obtained by the method disclosed above.

The present invention also provides a method of targeting and verifying a medical procedure using at least one computer system, wherein the at least one computer system has at least one processor. The method is performed by obtaining a three-dimensional scanned image of a patient, wherein the image includes at least one anatomical reference point, at least one external reference point, and at least one anatomical target point. From the image and using the at least one processor, location and orientation data of the at least one anatomical reference point, at least one external reference point, and at least one target point are obtained. From that data and using the at least one processor, a digital model of the at least one target point, at least one anatomical reference point, and at least one positioning interface device is obtained. Using the digital model, at least one processor, and a user interface, a user may input information for simulating a medical procedure.

In some embodiments, the three-dimensional scanned image may be obtained through a CT scan, a T1-weighted or T2-weighted MRI scan, or a PET scan.

In some embodiments, the anatomical point of the scanned image is a brain structure In non-limiting embodiments, the brain structure is the AC, PC, and/or MCP.

The digital model formed from the data of the scanned image may also contain stereotactic head ring mounts for the positioning interface devices as well as a stereotactic targeting device or fiducial registration device. Additionally, the digital model may also contain at least one surgical entry point.

In some embodiments, the step of simulating a medical procedure involves superimposing or placing the digital model on or in the scanned three-dimensional image.

In some embodiments, the method further includes a fabrication step, wherein the digital model is fabricated into a solid physical model. The solid physical model includes the at least one target point, at least one anatomical reference point, and at least one positioning interface device.

In some non-limiting embodiments, the medical procedure to be simulated is an irradiation procedure and further includes the step of obtaining dosimetry information on the digital model.

Also provided herein is a solid physical model obtained by the above method. In some non-limiting embodiments, the solid physical model further includes at least one of a gel, film, or sensor capable of detecting irradiation.

Also provided herein is a method of providing a unitary positioning interface for a medical device. The interface is non-invasive, meaning it does not need to be attached to a subject. The method is performed by implanting a plurality of detectable emitters in a patient's body and scanning the body, thereby producing a three-dimensional scanned image of the emitters and the body. The image includes at least one anatomical point within the body. From the image, location and orientation data relating to the emitters and the at least one anatomical point is determined. From that data, a digital model including a plurality of positioning interface devices and the location and orientation of the plurality of emitters and the at least one anatomical point is generated. The plurality of positioning interface devices includes a plurality of sensors that are capable of detecting the emission from the emitters. The digital model is organized such that the plurality of sensors is aligned with the emitters. From this digital model, a solid physical model of the unitary positioning interface is fabricated. The unitary positioning interface is organized such that the plurality of sensors is capable of alignment with the emitters in the patient's body.

In some embodiments, the three-dimensional scanned image may be obtained through a CT scan, a T1-weighted or T2-weighted MRI scan, or a PET scan.

In some embodiments, the anatomical point of the scanned image is a brain structure. In non-limiting embodiments, the brain structure is the AC, PC, and/or MCP.

Also provided herein is a unitary positioning interface, obtained by the above method.

The invention further provides a system for performing a medical procedure on a patient. The system includes a patient, wherein the patient has a plurality of emitters embedded in at least one body part. The emitters of the system have at least one position. The system also includes a unitary positioning interface. The unitary positioning interface includes a plurality of sensors, and those sensors have at least one position. The unitary positioning interface is in communication with a computerized control system such that data regarding the position of the sensors in relation to the position of the emitters is communicated from the unitary positioning interface to the computerized control system. The system also includes a medical device in communication with the computerized control system. The computerized control system transmits data regarding the position of the sensors in relation to the position of the emitters such that when the sensors are near to, or aligned with, the emitters, the medical device is capable of functioning, but that when the sensors are not near to the emitters, the device cannot function.

In certain embodiments, the medical device is capable of irradiating the patient. In other non-limiting embodiments, the medical device is an orthopedic device.

Also provided herein is a method of providing a unitary positioning interface for a stereotactic frame system. The method is conducted by implanting a plurality of anchors in a patient's body, scanning the patient's body and thus providing a scanned image of the body. The image will contain at least a portion of the implanted anchors and at least one anatomical point within the body. The method further includes determining, from the at least one image, location and orientation data relating to at least a portion of the anchors and the at least one anatomical point. At least a portion of this data is then inputted into a computer system. From the data, a digital model is then produced. In a subsequent step, a plurality of positioning interface devices are fabricated from the digital model.

In some embodiments, the anchors are detectable emitters, which may be passive or active. Further, the three-dimensional scanned image may be obtained through a CT scan, a T1-weighted or T2-weighted magnetic resonance imaging (MRI) scan, or a positron emission topography (PET) scan.

In some embodiments, the anatomical point of the scanned image is a brain structure. In non-limiting embodiments, the brain structure is the AC, PC, and/or MCP.

The digital model formed from the data of the scanned image may also contain stereotactic head ring mounts for the positioning interface devices as well as a stereotactic targeting device or fiducial registration device. Additionally, the digital model may also contain at least one surgical entry point.

The three-dimensional scanned image may also contain at least one target point within the body. When target data is included, a further step in the method may include calculating stereotactic frame settings for a medical procedure. The medical procedure in this embodiment may be directed at the at least one target.

In addition to fabricating a plurality of positioning interface devices, the fabricating step may also include fabricating a solid physical model of the target. In this way, the surgical procedure may be simulated with precision due to the specific positioning interface devices and the target drawn specifically to the area of interest of the patient. The fabricating may be by high-speed laser sintering or traditional machining. High-speed machining may also be utilized. In certain embodiments, the positioning interface devices are fixation posts for a stereotactic frame.

Also provided herein are positioning devices obtained by the method disclosed above.

DESCRIPTION OF THE PREFERRED EMBODIMENTS

Figure 1:
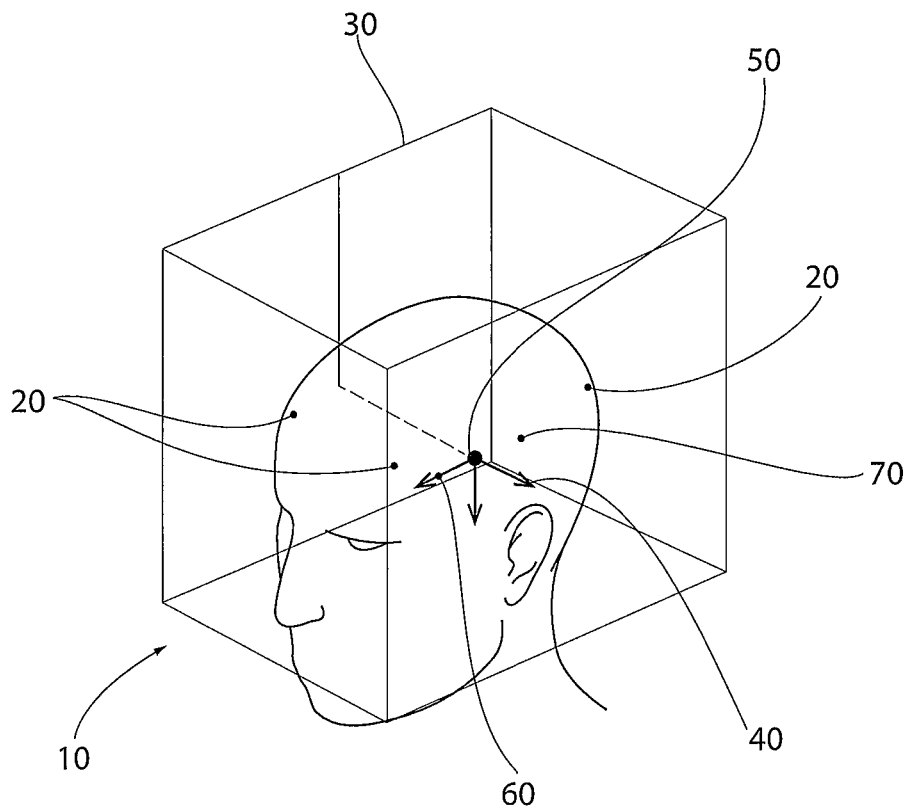
FIG. 1 is a perspective view of a three-dimensional scanned image showing alignment of the frame coordinate map (FCM) and patient reference map (PRM) of the present invention.

The following description is merely exemplary in nature and is in no way intended to limit the invention, its application, or uses.

The invention describes a method of providing customized positioning interfaces to place stereotactic frame systems more ideally for the intended use and patient. This is an advantage since it replaces the use of less than ideal standard adjustable fixation posts and pins with patient and procedure-customized fixation devices.

The invention uses bone anchors or detectable active or passive emitters implanted in advance of the planning as both a mounting system and as a patient to stereotactic system registration device. This allows patient registration and planning from a day to several weeks prior to the surgical procedure. This is not possible with current stereotactic frames and leads to patient discomfort over long waiting periods, to surgeons pressured into making rapid decisions about the surgical plan, and to inefficient scheduling of hospital resources.

Since the anchors or emitters may remain implanted after the initial surgical procedure and are still registered in the scans and to the stereotactic system, repeated applications of the stereotactic system are possible and do not require painful, expensive, and resource consuming head ring reapplication. Duplicate sets of the customized positioning interface devices, or fixation posts, may be used, or another set manufactured to refocus the stereotactic system for different targeting without rescanning. The use of permanently implanted emitters capable of being sensed by customized fixation devices will allow non-invasive re-application of the stereotactic device.

The invention incorporates surgeon inputs and planning to create these positioning interface structures, allowing them to place the stereotactic system perfectly for the intended surgical procedure. The system placement and targeting does not rely on inaccurate surgeon estimation of hidden anatomical references, but incorporates these references into the computed digital model. The digital model may then be fabricated to create a solid physical model.

These positioning interfaces or devices can be created in a planned shape to avoid interference with anatomy, areas of interest, and apparatus. They can also be provided with strengthening and stiffening structures or additional anchor points to increase accuracy that may be compromised due to the flexing or loosening of traditional fixation posts.

Since the stereotactic system is placed in perfect location and orientation, and the FCM can be perfectly aligned with a PRM calculated from the positioning of anatomical structures and the anchors, adjustment of frame settings for several targets can be done directly and does not require compensation for frame misalignment.

Unlike any other standard adjustable stereotactic frame method now used, the invention incorporates individual and specific patient anatomy of any desired complexity into its design. Since the anatomy is part of the model, it is easily displayed in the images of the patient for verification and for surgical planning.

Since the patient anatomy is part of the digital model, it can be realized and fabricated as a unitary object in itself, similar to a standard stereotactic "phantom", but made specifically for the patient and procedure, with individual patient structures and target points incorporated. It can then be used both for planning verification and for confirmation and adjustment of the frame settings during the surgical procedure based on actual patient anatomy.

In some embodiments, the digital model includes positions of other targets. For example, in non-limiting embodiments, the digital model includes patient anatomy for providing a properly scaled and aligned patient image and further includes tumor locations. In this way, the "phantom" can be utilized not only for surgical procedures, but also for dosimetry, so that a user may plan for irradiation dosing procedures and be able to calculate the precise amount of irradiation that may be directed to a certain part of the brain, increasing patient safety.

While the invention basically describes the creation of positioning interfaces, also referred to as fixation posts or fixation devices to place a stereotactic frame head ring in a known ideal position, there is no reason that more parts of the stereotactic frame, or substitute parts of similar function but customized shape better suited to the procedure, could not be part of the model developed by the planning system.

The positioning interface devices or fixation posts can be designed to hold related flexible portions of the body, such as the neck, shoulders or limbs, in a known and planned position relative to a scanned position to allow treatment based on a scanned position.

The computerized digital model, the computerized planning system and surgical planning software to display the images and select the critical points needed to allow the model to create the customized fixation posts are part of the invention. A computer based control system designed to trigger and stop treatment based on sensor emitter pairs signaling desired positions of related portions of the body is also part of the invention.

A standard stereotactic frame includes fixation posts and pins. In the method of the present invention, a patient is implanted with a plurality of anchors. In a preferred, non-limiting embodiment, the anchors are implanted in the cranium and are positioned in the same general areas used by standard fixation post pins, such as those provided by Leksell. Past use of these type of anchors has proved this is a less traumatic process for the patient. Following implantation, the patient is scanned to produce a three-dimensional image. The three-dimensional image includes at least a portion of the anchors and at least one anatomical point within the body.

In non-limiting embodiments, the anchors are detectable emitters. Emitters of this type may be either active or passive. In a non-limiting embodiment, the emitters are radiopaque. The anchors, or emitters, may be made of any suitable material, based on the scan type needed and the procedure desired.

In further non-limiting embodiments, the scan utilized to obtain the three-dimensional image is a CT scan, a T1-weighted MRI scan, a T2-weighted MRI scan, or a PET scan. In non-limiting embodiments, the anatomical points in the anatomical points obtained in the scan are the anterior commissure (AC), posterior commissure (PC), and the location of a point on the mid-sagittal plane (MP) to determine the patient reference map (PRM) originating at the mid-commissural point (MCP).

From the scanned image, location and orientation data relating to at least a portion of the anchors and the at least one anatomical point are determined. In some embodiments, the locations of anatomical targets and entry points for surgery or other medical treatments or procedures, and other anatomical structures will be determined.

From this data, using a computerized planning system and a standardized frame coordinate map (FCM), the frame mid point (100,100,100) will be virtually positioned exactly at the at least one anatomical point. In some embodiments, the FCM is virtually positioned exactly at the MCP.

The computerized planning system will then rotate the FCM about the anatomical point until the FCM exactly coincides with the PRM. In non-limiting embodiments, the FCM is positioned at another anatomical location and orientation relative to the PRM that is more suitable for a given treatment protocol.

From the data, a computer customizable digital model comprising a plurality of positioning interface devices, the PRM, the FCM, and the location and orientation of at least a portion of the plurality of anchors and the at least one anatomical point is generated. In some embodiments, the positioning interface devices are fixation posts with changes to allow mounting to an anchor screw and standoff similar to those used in other customizable fixtures (such as, for example, the FHC STarFix microTargeting Platform) instead of a Leksell pin. These fixation posts may be provided in the computerized planning system. In some embodiments, the digital model includes the relative locations of head ring mounts for the positioning interface devices.

In non-limiting embodiments, the locations of at least one target within the body and entry points and other anatomical positions are entered into the model. In some non-limiting embodiments, the entry points are surgical entry points. Using a suitable anchor scan, (preferably a CT scan for accuracy), loaded into the computerized planning system, the scan coordinates of these patient specific critical points are determined. The patient specific anchor coordinates, plus the AC, PC, and MCP or MP, and the optional locations are entered into the digital model. In non-limiting embodiments, several scans containing the at least a portion of the anchors and at least one anatomical point are merged or registered to each other to determine the critical point relative locations.

The computerized planning system will create the required shape of a digital model of a plurality of positioning interface devices to connect the anchors to stereotactic frame head ring mounting points. In a preferred, non-limiting embodiment, the digital model comprises four positioning interface devices to be connected to four stereotactic frame head ring mounting points. The digital model of the fixation posts are fixed in shape by the required design inputs and have no adjustable slots like standard positioning interface devices, but instead have fixed mounting holes corresponding to the head ring mounting positions. If additional anatomical points are entered into the computerized planning system, the positioning interface devices could also be formed to avoid blocking areas of interest that standard positioning interface devices cover and could have interconnecting structures to make them very rigid, including secondary anchor points. They avoid interference with anatomy or scanning structures, and are very close fitting.

The digital model of these virtual patient and procedure specific positioning interface devices can be displayed in the computerized planning system in place on the patient with a virtual head ring in two-dimensional and three-dimensional views. In non-limiting embodiments, the adjustable stereotactic devices and standard fiducial system for the stereotactic frame or a Gamma Knife® attachment is virtually displayed in the images. This allows surgeon inspection of the proposed positioning interface device set and allows visualization and planning of the procedure. In this way, the surgeon can review the placement of the actual head ring and fiducial device. In non-limiting embodiments with specific target locations available in the model, the frame settings or radiotherapy device settings required to reach these locations through specific entry points are computed and virtually rehearsed.

In non-limiting embodiments, in addition to the digital model of the positioning interface devices, a digital model of the target locations can be computed using the same anchor location and orientation data and any other critically identified points. This model consists of points or of segmented and rendered anatomical structures. This digital model is used for target and surgical equipment verification prior to surgery, as a targeting "phantom". The phantom could also be displayed in the patient anatomy in the scan images. The ability to display and utilize a patient specific customized phantom with anatomical references both in the images and prior to surgery is unique, and assists the surgeon in planning a surgical route and verifying the targeting data. Displaying the phantom in the images in the anatomy of the patient verifies its design during planning, just as the positioning interface devices are verified. When displayed together against scan images, they allow visualization of the surgical procedure and targeting not possible before. Moreover, a customized "phantom" allows for verification of the scanned images utilized for the formation thereof. This is particularly important when multiple scanned images are utilized in planning a surgical procedure.

In further non-limiting embodiments, the digital model further comprises information relating to tumor or non-tumor sites which are posited to be the target of irradiation. In this way, given precise location data possible through the use of the customized "phantom", dosimetry can be calculated and allow for increased patient safety in such sensitive and critical medical procedures. The customizable "phantom" will allow for precise coordinate measurements, distance measurements, volume measurements, and irradiation dose. In terms of dose, optimal absolute dose, relative dose, and point dose information may be obtained and utilized in later medical procedures.

When the surgeon is satisfied with the planning and the digital model displayed, he or she saves the model. The subsequent step is fabricating, from the digital model, a solid physical model including a plurality of positioning interface devices. In non-limiting embodiments, the solid physical model includes a solid physical model of the target structure, or a "phantom". Fabrication may be achieved by any suitable method for the production of a solid physical item. In non-limiting embodiments, the fabrication is accomplished through selective laser lintering, high speed machining, or any of a number of other high speed techniques. The solid physical model may be manufactured in polymer, metal, or whatever material may be suitable for the specific procedure.

When these positioning interface devices are attached to the head ring of a stereotactic frame and the head ring is applied to the patient, the head ring will be in the ideal pre-planned position on the patient and, unlike current procedures, no scan with the head ring attached need be done, since the anchor scan fulfills that purpose and completes the patient to frame registration.

At a minimum, the method provides an ideal location of a stereotactic frame where common anatomical atlases exactly correspond with the frame position. What it also does is eliminate the need to scan the patient with the head ring in place on the morning of the procedure. The scan may be done from a day to several weeks in advance. It also allows the planning for a stereotactic procedure such as Gamma Knife® radiosurgery or deep brain stimulation to be carefully and thoughtfully done based on the anchor scan alone, with stereotactic frame settings for targeting known in advance of frame placement, since the registration has been done with the anchors. For procedures that require repeated attachment of the frame, the anchors may remain in place under the skin of the patient and the customized positioning interface devices can be resterilized or provided in duplicate sets. The anchors may be designed to be flush with the skull and be permanently implanted to allow repeated applications over a period of years. Unlike current practice, no reapplication of Leksell standard fixation posts and head ring and rescanning is required. As such, the method advantageously reduces pain and anxiety for the patient, and increases the precision with which a surgeon or other medical technician may complete a given task.

In further non-limiting embodiments, the customized "phantom" that is fabricated is utilized in a stereotactic frame for simulation of a medical procedure. This simulation may include surgery, irradiation, or any medical procedure where precise localization is critical. In other non-limiting embodiments, the solid physical model customized "phantom" is utilized for dosimetry. The solid physical model may include sensors, gels, and/or films capable of detecting and quantifying irradiation levels. The solid physical model customized "phantom" is inserted into a frame through connection with the customized fixation posts and is irradiated. The sensors provided therein allow for dosimetry studies to adjust levels to which a patient is exposed, and to verify targeting. The sensor may communicate the information through direct connection with a computer system, through wide area network (WAN), or such information may be stored with the sensors which may later be placed into communication with a computer system for analysis of dosimetry information.

Also provided by the invention are a plurality of positioning interface devices obtained by the above method. These devices may be customized fixation posts for use in a Leksell stereotactic frame. The devices may be made of any suitable material, such as metals, alloys, polymers, or the like.

Also provided herein is a method of targeting and verifying a medical procedure. The method is performed on at least one computer system, wherein the at least one computer system has at least one processor. The method is performed by obtaining at least one three-dimensional scanned image of a patient. The image may be obtained by any suitable method known to those in the technology. In non-limiting embodiments, the scanned image is obtained by use of a CT scan, T1 or T2-weighted MRI scan, or PET scan.

The scanned image contains at least one anatomical reference point and one anatomical target point inside the patient, and at least one external reference point. In non-limiting embodiments, the at least one external reference point is at least one anchor embedded in the patient's body. The anchors, or emitters, may be made of any suitable material, based on the scan type needed and the procedure desired. In non-limiting embodiments, the at least one anchor is embedded in the patient's skull. In further non-limiting embodiments, the at least one anchor is a detectable emitter that is either passive or active. In preferred non-limiting embodiments, the detectable emitter is radiopaque.

Using the at least one processor, location and orientation data relating to the at least one anatomical reference point, at least one target point, and at least one external reference point are determined from the at least one scanned image. Using the at least one processor, a digital model comprising the at least one target point, at least one anatomical reference point, and at least one positioning interface device is generated.

Using the digital model comprising the at least one target point, at least one anatomical reference point, and at least one positioning interface device, a user may, by use of an interface with the at least one computer system, simulate a medical procedure on the at least one target of the digital model. In non-limiting embodiments, the medical procedure is a surgical procedure. In further non-limiting embodiments, the medical procedure is neurosurgery and the at least one target is a brain structure. In further non-limiting embodiments, the medical procedure is an irradiation procedure, such as a Gamma Knife® procedure.

In a preferred, non-limiting embodiment, the simulating step also includes superimposing or otherwise displaying the digital model of the at least one target point, at least one anatomical reference point, and at least one positioning interface device on or with the at least one scanned three-dimensional image.

In a preferred, non-limiting embodiment, the method further comprises fabricating a solid physical model of the at least one target point, at least one anatomical reference point, and at least one positioning interface device. In this way, a user may simulate the medical procedure on the solid physical model, and not solely on the digital model. The at least one positioning interface device, in non-limiting embodiments a plurality of fixation posts, may be removably attached to a stereotactic frame, and the accuracy of the measurements may be verified on the solid physical model. The solid physical model may be made of any suitable material, such as metals, alloys, polymers, or the like.

Also provided herein is a solid physical model obtained by the above method, the solid physical model including the at least one target point, at least one anatomical reference point, and at least one positioning interface device. The solid physical model may be made of any suitable material, such as metals, alloys, polymers, or the like.

Also provided herein, and more suited to radiosurgical use, though useable in other stereotactic procedures, is a method of providing a unitary positioning device that is non-invasive. In this method, a plurality of anchors or mounting locations are implanted emitters, either active or passive, that are surgically placed in the bone of the targeted area. The anchors, or emitters, may be made of any suitable material, based on the scan type needed and the procedure desired. In non-limiting embodiments, the emitters are implanted permanently in the patient, allowing for repeated treatment regimens. In further non-limiting embodiments, the emitters are implanted in the patient's skull. In preferred non-limiting embodiments, the emitters are active or passive. In further preferred, non-limiting embodiments, the emitters are radiopaque. The emitters are implanted in locations best suited to support the patient's specific body area of interest. In non-limiting embodiments, the emitters are implanted in the head and neck area. In further non-limiting embodiments, the wounds from the implantation are allowed to heal. These emitters need not be in a standard configuration or be placed in specific locations. A three-dimensional scanned image of the body is then obtained, the image including at least one anatomical point and the emitters. The scan may be obtained by any suitable method known to those in the art. In non-limiting embodiments, the scanned image is obtained by use of a CT scan, T1 or T2-weighted MRI scan, or PET scan.

The scanned image of the patient's body includes the emitters, and location and orientation data of the emitters and the at least one anatomical point are determined. This data is used to generate a digital model of a plurality of positioning interface devices, the devices bearing a plurality of sensors. In non-limiting embodiments, the positioning interface devices are sensor-bearing fixation posts adapted for interaction with a head ring mount for a stereotactic frame. The digital model is designed such that sensors in the plurality of positioning interface devices are aligned with the plurality of emitters in the patient's body. A solid physical model of the unitary positioning interface, which includes the plurality of sensor-bearing positioning interface devices, is then fabricated from the digital model, the unitary positioning interface formed in such a manner that a patient may comfortably be positioned so that the sensors of the unitary positioning interface are aligned with the emitters in the patient's body. The unitary positioning interface may be made of any suitable material, such as metals, alloys, polymers, or the like.

In non-limiting embodiments, a patient-specific head-holding fixture or a holder for other parts of the body is custom designed to place sensors over or proximal to the emitters previously placed in the body. From the digital model, customized by incorporating the emitter locations and other critical anatomical inputs, information sufficient to produce the patient specific sensing positioning interface devices or head holder using rapid manufacturing techniques is generated. This information is input to a rapid manufacturing machine, and the custom device or devices built.

Also provided herein is a system for performing a medical procedure on a patient. For repeated stereotactic procedures, or for non-invasive procedures, the patient is placed, non-invasively, in the head ring with the sensing positioning interface devices or in a custom-built sensing head holder of similar principles. The patient has already had emitters implanted in his or her body, and has had a customized unitary positioning interface fabricated, for example, according to the above method. This head ring or holder contains custom-positioned embedded or attached sensors designed to sense the proximity of the emitters in the patient's body and to transmit the relationship to a control system. The control system may be a stand-alone device, and thus capable of interaction with existing medical equipment. In non-limiting embodiments, the control system is present in the treatment device. In non-limiting embodiments, the treatment device is a device capable of irradiation, such as a Gamma Knife®.

As the patient is placed non-invasively in the unitary positioning interface, in non-limiting embodiments a head-holder, the control system is in communication with the positioning interface and the device. The control system transmits data and does not allow treatment to be triggered unless the proximity of the sensors to the emitters was such that the head or treated area was in a pre-planned location and orientation to a specific degree of precision. In preferred, non-limiting embodiments, at least three and preferably four or more implanted emitters and corresponding sensors in the custom manufactured posts or head holder are used to determine the orientation and location of the treated area in the head. More emitters and sensors may be implanted and fabricated if treating flexible or jointed areas of the body, such as the spine or limbs. In such areas, the custom holding or positioning device assures that the flexible parts of the body are constrained in either the same position that the body was in during the scan, or in a desired known calculated position relative to that scanned position.

In non-limiting embodiments, the aforementioned is used for treatment of the cervical neck and spine in the Gamma Knife® or similar devices. The problem of fixating the neck and spine relative to the head is addressed by using a combination of anchors/attachments and emitter/sensor pairs in the body and in the unitary positioning interface or custom head holder, to be used with the above control system. The head is held by the anchored or sensor placed fixation posts or head holder, and previously placed emitters or anchors in the upper spine or bones of the shoulder and neck area signal the position of the neck and upper spine. The customized interface device or head holder uses extensions planned in the solid physical model based on the anchor or emitter locations to place sensors or anchor attachments at or proximal to the desired positions of the implanted anchors or emitters in the body. These extensions may, for example, be part of the unitary device extending from the base ring mounting locations in an opposite direction from the upper portion of the posts that mate with the head locations, and extend down to the neck and shoulder area. Treatment is triggered by a signal from the emitter/sensor pairs indicating correct positioning of the neck and spine relative to the head based on the scanned position used to plan the treatment. Any movement of the neck or spine out of the desired treatment position stops the therapy. Alternatively, when using only anchors and attachment pairs, the neck is physically constrained from moving from the desired position.

This embodiment describes the use of the invention with the Elekta Leksell stereotactic frame, either for Gamma Knife® surgeries, or when using the Leksell stereotactic arc system, but it will be obvious that any stereotactic device or frame that relies on scanning the patient with a fiducial ring in place would benefit from this invention. As such, this invention is not to be limited to use in a Leksell stereotactic frame or Gamma Knife®.

Turning to the appended figures, in which like numbers indicate like elements throughout, FIG. 1 provides a perspective view of a three-dimensional scanned image 10 of an embodiment of the present invention. Note that while for demonstrative purposes the figures depict implantation into and medical procedures performed on a human head, the invention provided herein may be utilized in any medical technology where precision is required, including orthopedic procedures, irradiation procedures, and surgical procedures, amongst many non-limiting examples.

A patient (not numbered) is implanted with a plurality of emitters or anchors 20. Such implantation occurs in the skull. In instances where customized fixation posts are to be fabricated, the patient has anchors 20 embedded in the skull. The anchors 20 are preferably radiopaque, but in any event detectable in a scanned three-dimensional image produced through any suitable type of imaging including T1 and T2-weighted MRI, CT, and PET.

In instances where fixation posts are not fabricated and non-invasive techniques are contemplated, emitters 20 may be implanted. These emitters may be passive or active or the emitters may act as triggers for sensors or other devices built into external devices, for example a customized fixture produced according to the present invention. In non-limiting embodiments, the emitter requires no power source, and is powered by proximity to an external device, for instance an irradiation or orthopedic device or a customized fixture produced according to the present invention. In non-limiting embodiments they are radiopaque. In other non-limiting embodiments the emitter is a radio-frequency identification (RFID)-based emitter. In other non-limiting embodiments the emitter is an ultrasonic emitter, for example as disclosed in U.S. Pat. No. 7,857,766. In other non-limiting embodiments the emitter is a magnetic resonance-compatible emitter, such as that disclosed in U.S. Pat. No. 5,016,639.

Referring further to FIG. 1, upon implantation of anchors or emitters 20, the patient is scanned utilizing any suitable scanning technology. The scan detects anchors or emitters 20 and at least one anatomical point within the subject. In non-limiting embodiments, the anatomical points include the anterior commisure 60 and posterior commisure 70. Utilizing the positions of the anchors or emitters 20 and the anatomical points, a patient reference map 40 is generated. In non-limiting embodiments, the patient reference map (PRM) originates at the mid-commissural point (MCP) 50.

The three-dimensional scanned image of FIG. 1 may then be manipulated by a user on any suitable computer system. A user may input a standardized frame coordinate map (FCM) 30 and manipulate the FCM 30 so that the FCM 30 is aligned with the at least one anatomical point 60, 70. The FCM 30 is then rotated so that it coincides with the PRM 40. In non-limiting embodiments, the FCM 30 is aligned with the MCP 50 prior to rotation to align with the PRM 40.

Figure 2:
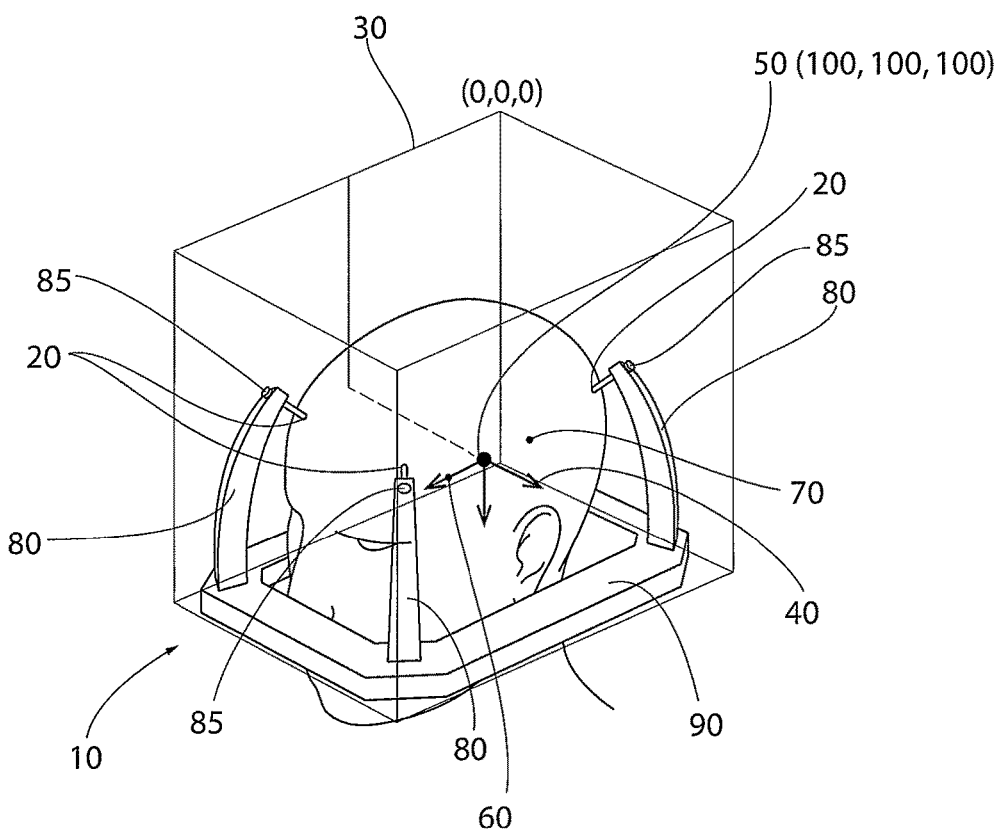
FIG. 2 is a perspective view of the PRM and FCM and virtual customized positioning interface devices according to FIG. 1.

Turning to FIG. 2, utilizing at least a portion of the data from the FCM 30, PRM 40, anchors or emitters 20, and the at least one anatomical point (for example, 60, 70), virtual positioning interface devices 80 may be introduced into the model produced from the scanned images. The FCM may have coordinates as in a typical three-dimensional coordinate system. In some non-limiting embodiments, the FCM has an origin at (0, 0, 0) and the MCP is at (100, 100, 100).

The devices 80 are customized based on patient anatomy generated from the scanned images. For the digital model produced from the data, customized interface devices 80 may also include a virtual standardized stereotactic frame ring 90. The virtual model includes virtual removable connections between virtual customized positioning interface devices 80 and virtual standardized stereotactic frame ring 90.

Figure 4:
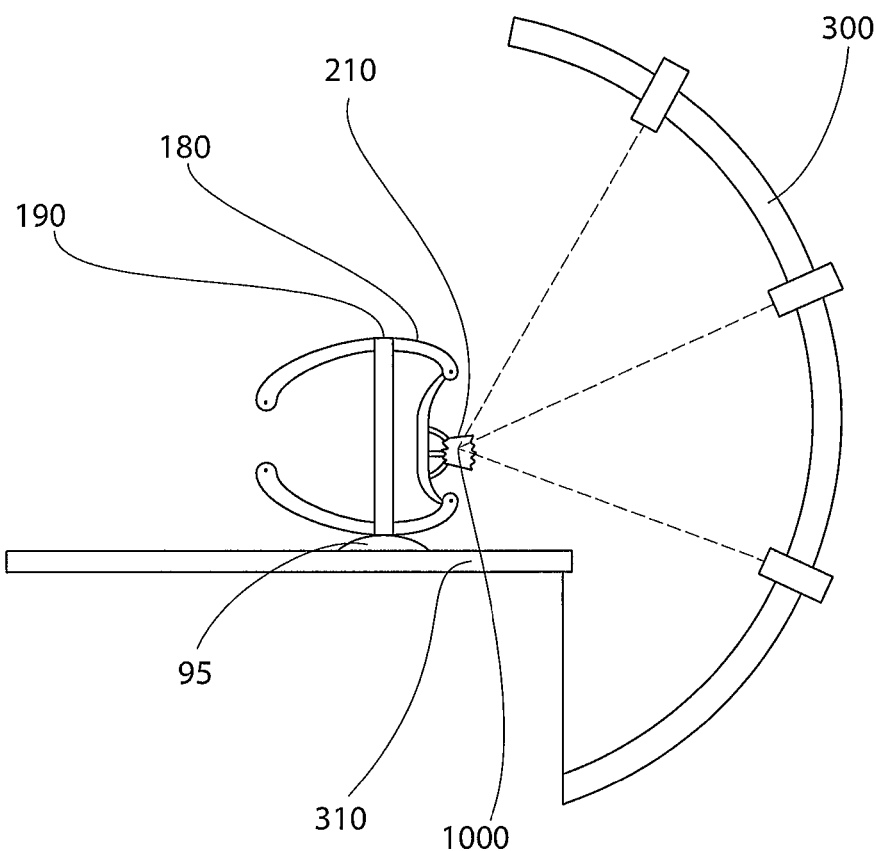
FIG. 4 is a side view of a simulation of a medical procedure utilizing customized positioning interface devices and a solid physical-model customized "phantom" according to one embodiment of the present invention.
Figure 5:
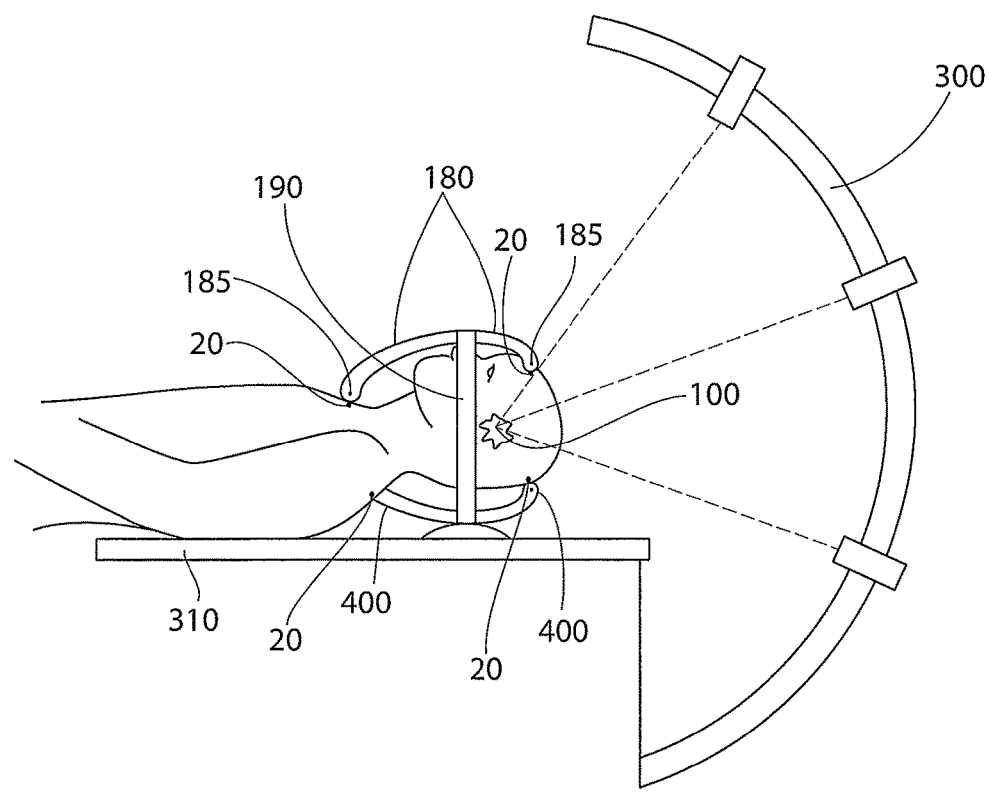
FIG. 5 is a side view of a medical procedure utilizing customized positioning interface devices according to one embodiment of the present invention.

Utilizing the digital model described above and depicted in FIG. 2, solid physical models may be fabricated from any suitable material. In non-limiting embodiments, the solid physical model is fabricated through selective laser sintering or high-speed machining. An example of such a solid physical model is illustrated in FIGS. 4-5. In this way, customized interface devices 180 are fabricated and may be removably attached to the anchors 20 implanted in the patient's body. Customized interface devices 180 may be connected to anchors 20 through any suitable means for attachment 185. In non-limiting embodiments, standardized screws are utilized to connect customized interface devices 180 to anchors 20 implanted in the patient. The customized interface devices 180 are fabricated in such a way that they provide for customized targeting and simple, reliable attachment to a standardized stereotactic head frame ring 190.

Figure 3:
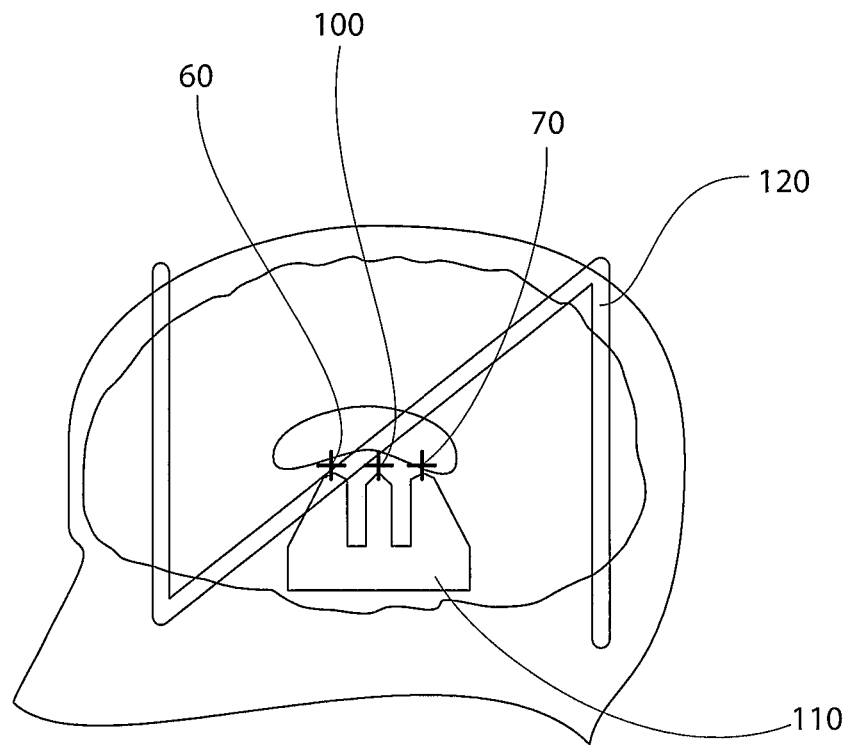
FIG. 3 is a side view of the virtual customized "phantom", virtual fiducial frame bars, and scanned brain image according to one embodiment of the present invention.

Turning, to FIG. 3, utilizing the digital model formed from the data of the anchors 20, at least one anatomical point (for example 60, 70), and the FCM 30 and PRM 40, a virtual "phantom" 110 may be produced. The virtual phantom 110 may include a plurality of anatomic points (for example anterior commissure 60, posterior commissure 70), and may additionally include at least one target 100 that is to be the focus of a medical procedure. The digital model may further include virtual fiducial stereotactic frame bars 120 for use in verifying positioning and targeting for a medical procedure directed at the at least one target 100. The digital model, including virtual "phantom" 110, may be used for simulating a medical procedure.

Turning to FIG. 4, as with the virtual customized positioning interface devices 80, a solid physical customized "phantom" 210 of the virtual customized "phantom" 110 may also be fabricated through any suitable means. In non-limiting embodiments the customized phantom 210 is fabricated through selective laser sintering or high-speed machining. The customized phantom 210 may include at least one target 1000 that allows for verification of targeting, and for simulation of a medical procedure. In a non-limiting embodiment, the medical procedure is an irradiation procedure. With reference to FIG. 4, an irradiation device 300 and table or platform 310 for use therein are provided. The customized "phantom" 210 as well as customized positioning interface devices 180 are also provided, and through interaction with each other, and of devices 180 with stereotactic head frame ring 190, are secured to table or platform 310 by any suitable means 95. In non-limiting embodiments, the head frame ring 190 is secured to table or platform 310 through use of standardized screws. In FIG. 4, it can be appreciated that the customized "phantom" 210 including at least one target 1000 may be irradiated, mimicking a medical procedure. In non-limiting embodiments, customized "phantom" 210 includes means for detecting and evaluating or quantifying the dose of radiation received from device 300 for use in dosimetry. In non-limiting embodiments, detection is achieved through sensors, gels, films, or the like.

Turning to FIG. 5, the customized positioning interface devices 180 may be utilized in a medical procedure as illustrated. This may occur after verification of dose and targeting through use of the customized "phantom" 210, as described above and shown in FIG. 4. With reference to FIG. 5, in non-limiting embodiments an irradiation device 300 and table or platform 310 for use therein are provided. Patient is placed on platform or table 310 and if customized positioning interface devices 180 are provided, patient may be attached to devices 180 through removable connection with implanted anchors 20 by any suitable means for attachment 185. Devices 180 may then be removably connected to a standardized stereotactic head frame ring 190, which may be removably connected to table or platform 310. Irradiation may be focused on target 100, which may or may not be previously verified for location and dose through use of the customized "phantom" 210 as illustrated in FIG. 4.

In non-limiting embodiments, platform or table 310 is an integral positioning table that is part of irradiation device 300. In such a non-limiting embodiment, the table 310 and irradiation device 300 are an integral system and the patient is positioned appropriately on the table 310 based on the FCM. In this way, the customized positioning interface device 180, table 310, and irradiation device 300 function seamlessly to align the patient and communicate proper or improper alignment for initiation, continuation, and cessation of a medical procedure. The non-invasive aspects of this embodiment reduce patient discomfort and stress.

Figure 9:
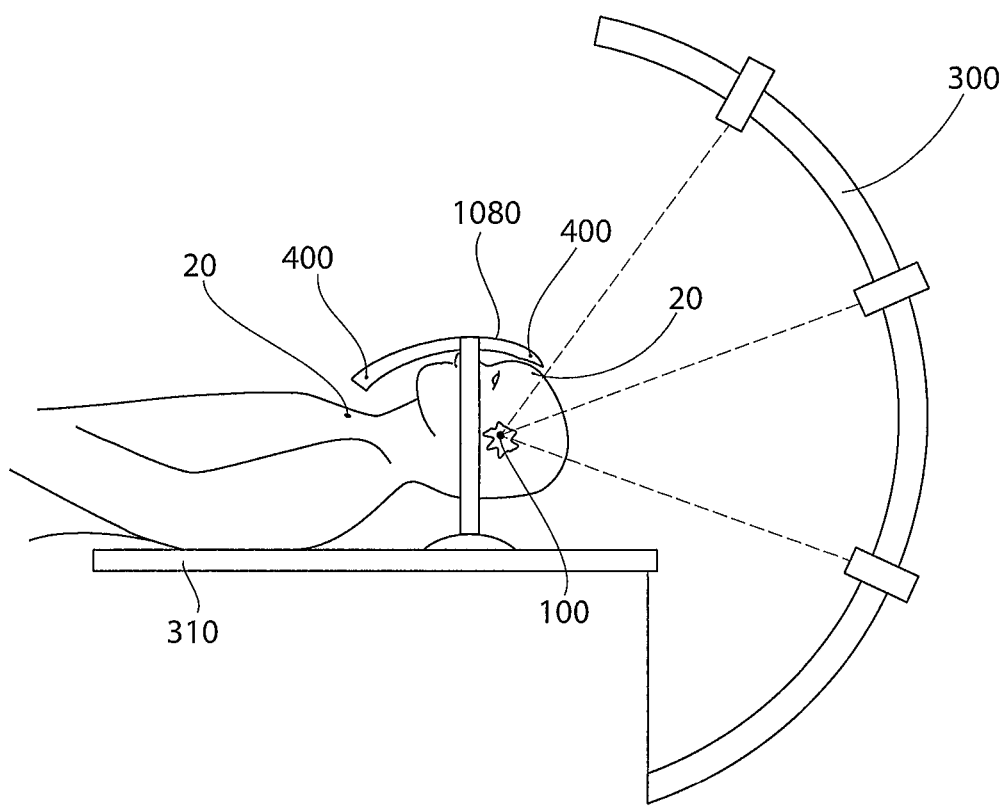
FIG. 9 is a side view of a medical procedure utilizing a customized non-invasive positioning interface according to one embodiment of the present invention.

In non-limiting embodiments, for example, as illustrated in FIG. 9, a non-invasive positioning device 1080 is provided. Such a device is obtained in a similar manner as the customized positioning interface devices 180. However, such a non-invasive device 1080 may be unitary in construction and may not be invasive. More specifically, such a device 1080 need not be attached to the patient. In non-limiting embodiments, non-invasive device 1080 is provided with sensors 400 and fabricated in such a manner that sensors 400 may be aligned with emitters 20 implanted in the patient.

These emitters 20 may be passive or active or the emitters may act as triggers for sensors or other devices built into external devices, for example a non-invasive position device 1080 or customized fixture produced according to the present invention. In non-limiting embodiments, the emitter requires no power source, and is powered by proximity to an external device, for instance an irradiation or orthopedic device or a customized fixture produced according to the present invention. In non-limiting embodiments they are radiopaque. In other non-limiting embodiments the emitter is an RFID-based emitter. In other non-limiting embodiments the emitter is an ultrasonic emitter, for example as disclosed in U.S. Pat. No. 7,857,766. In other non-limiting embodiments the emitter is a magnetic resonance-compatible emitter, such as that disclosed in U.S. Pat. No. 5,016,639.

Non-invasive device 1080 may be in communication with the computer system (not shown) controlling medical device 300, for example, an irradiating device. Sensors 400 may provide data as to location and orientation in relation to emitters 20, and the computer system utilizes such data to communicate to device 300 whether the procedure may be begun, or whether it may continue. If the patient shifts or is moved such that emitters 20 are not proximal to sensors 400, that data is communicated to the computer system and shuts off device 300, ensuring precision and safety in a medical procedure in a non-invasive manner.

In other non-limiting embodiments, the non-invasive positioning device 1080 may be utilized in other medical procedures, for example in those involving orthopedics. Those skilled in the art will recognize that the inventions described herein, particularly the non-invasive device 1080, may be utilized in any medical manner that requires precision of localization. In non-limiting embodiments, such a device 1080 may be utilized in knee or hip replacement surgeries. Implanted emitters 20 and sensors 400 may be used to verify proper orientation and positioning of limbs following replacement of such joints.

Figure 6:
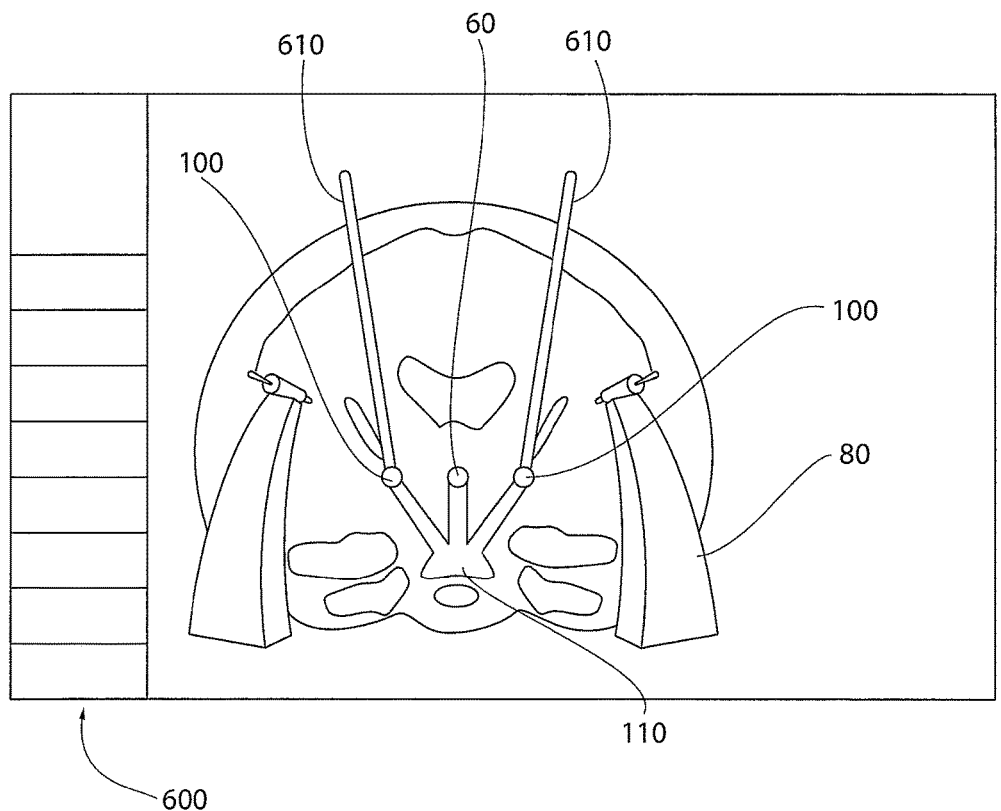
FIG. 6 is a depiction of the computer workspace of the computerized planning system showing a customized phantom, virtual customized positioning interface devices, and a virtual medical procedure according to one embodiment of the present invention.

Turning to FIG. 6, provided is a depiction of a possible computerized workspace 600 for use in an embodiment of the present invention. The workspace 600 may be utilized to form the digital model incorporated from the FCM 30, PRM 40, anchors or emitters 20, at least one anatomical point (such as AC, 60), and in non-limiting embodiments, at least one target 100. A digital model may be utilized to form virtual customized positioning interface devices 80 and virtual customized "phantom" 110. A medical procedure may be simulated in the digital model using the workspace 600. In non-limiting embodiments, a surgical procedure is simulated utilizing probes 610 or other surgical tools designed for use in precision surgeries.

Figure 7:
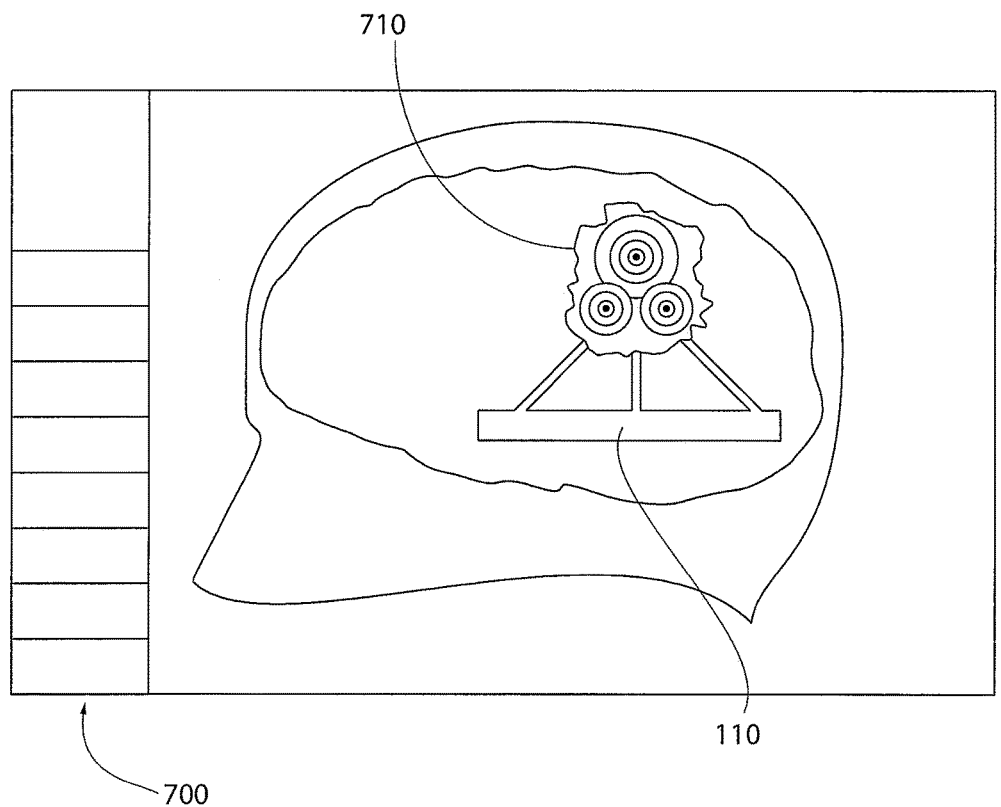
FIG. 7 is a side view of the virtual customized "phantom" for use in a medical procedure according to one embodiment of the present invention.

In other non-limiting embodiments, illustrated in FIG. 7, simulation of irradiation or other medical procedures may be carried out using workspace 700, and may include dosimetry. The digital model may or may not utilize three-dimensional scanned images of the patient. In this non-limiting embodiment, "phantom" 110 may include tumor 710 information for use in planning radiation therapy. This planning may include precision localization, dosimetry, and the like.

Figure 8:
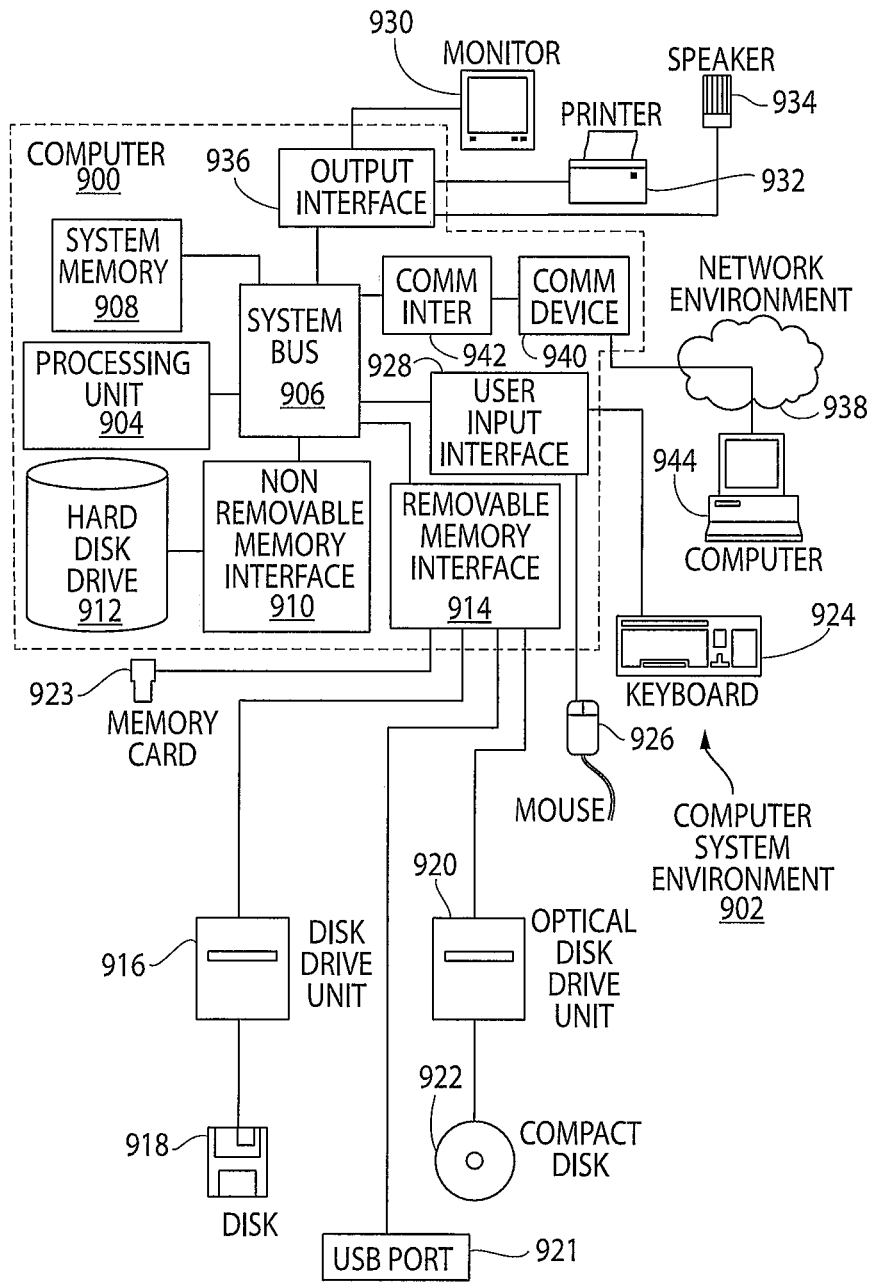
FIG. 8 is a diagram of a computing system environment for use in the present invention.

The present invention may be implemented on a variety of computing devices and systems, wherein these computing devices include the appropriate processing mechanisms and computer-readable media for storing and executing computer-readable instructions, such as programming instructions, code, and the like. As shown in FIG. 8, personal computers 900, 944, in a computing system environment 902 are provided. This computing system environment 902 may include, but is not limited to, at least one computer 900 having certain components for appropriate operation, execution of code, and creation and communication of data. For example, the computer 900 includes a processing unit 904 (typically referred to as a central processing unit or CPU) that serves to execute computer-based instructions received in the appropriate data form and format. Further, this processing unit 904 may be in the form of multiple processors executing code in series, in parallel, or in any other manner for appropriate implementation of the computer-based instructions.

In order to facilitate appropriate data communication and processing information between the various components of the computer 900, a system bus 906 is utilized. The system bus 906 may be any of several types of bus structures, including a memory bus or memory controller, a peripheral bus, or a local bus using any of a variety of bus architectures. In particular, the system bus 906 facilitates data and information communication between the various components (whether internal or external to the computer 900) through a variety of interfaces, as discussed hereinafter.

The computer 900 may include a variety of discrete computer-readable media components. For example, this computer-readable media may include any media that can be accessed by the computer 900, such as volatile media, non-volatile media, removable media, non-removable media, etc. As a further example, this computer-readable media may include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 900. Further, this computer-readable media may include communications media, such as computer-readable instructions, data structures, program modules, or other data in a modulated data signal, such as a carrier wave or other transport mechanism and include any information delivery media, wired media such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The computer 900 further includes a system memory 908 with computer storage media in the form of volatile and non-volatile memory, such as ROM and RAM. A basic input/output system (BIOS), with appropriate computer-based routines, assists in transferring information between components within the computer 900 and is normally stored in ROM. The RAM portion of the system memory 908 typically contains data and program modules that are immediately accessible to or presently being operated on by processing unit 904, e.g., an operating system, application programming interfaces, application programs, program modules, program data, and other instruction-based computer-readable codes.

With continued reference to FIG. 8, the computer 900 may also include other removable or non-removable, volatile or non-volatile computer storage media products. For example, the computer 900 may include a non-removable memory interface 910 that communicates with and controls a hard disk drive 912, i.e., a non-removable, non-volatile magnetic medium; and a removable, non-volatile memory interface 914 that communicates with and controls a magnetic disk drive unit 916 (which reads from and writes to a removable, non-volatile magnetic disk 918) an optical disk drive unit 920 (which reads from and writes to a removable, non-volatile optical disk 922, such as a CD ROM); a Universal Serial Bus (USB) port 921 for use in connection with a removable memory card, etc. However, it is envisioned that other removable or non-removable, volatile or non-volatile computer storage media can be used in the exemplary computing system environment 902, including, but not limited to, magnetic tape cassettes, DVDs, digital video tape, solid state RAM, solid state ROM, etc. These various removable or non-removable, volatile or non-volatile magnetic media are in communication with the processing unit 904 and other components of the computer 900 via the system bus 906. The drives and their associated computer storage media discussed above and illustrated in FIG. 8 provide storage of operating systems, computer-readable instructions, application programs, data structures, program modules, program data, and other instruction-based computer-readable code for the computer 900 (whether duplicative or not of this information and data in the system memory 908).

A user may enter commands, information, and data into the computer 900 through certain attachable or operable input devices, such as a keyboard 924, a mouse 926, etc., via a user input interface 928. Of course, a variety of such input devices may be utilized, e.g., a microphone, a trackball, a joystick, a touchpad, a touch-screen, a scanner, etc., including any arrangement that facilitates the input of data, and information to the computer 900 from an outside source. As discussed, these and other input devices are often connected to the processing unit 904 through the user input interface 928 coupled to the system bus 906, but may be connected by other interface and bus structures, such as a parallel port, game port, or a universal serial bus (USB). Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the computer 900 through an output interface 936 coupled to the system bus 906. It is envisioned that any such peripheral output devices may be used to provide information and data to the user.

The computer 900 may operate in a network environment 938 through the use of a communications device 940, which is integral to the computer or remote therefrom. This communications device 940 is operable by and in communication with the other components of the computer 900 through a communications interface 942. Using such an arrangement, the computer 900 may connect with or otherwise communicate with one or more remote computers, such as a remote computer 944, which may be a personal computer, a server, a router, a network personal computer, a peer device, or other common network nodes, and typically includes many or all of the components described above in connection with the computer 900. Using appropriate communication devices 940, e.g., a modem, a network interface or adapter, etc., the computer 900 may operate within and communicate through a local area network (LAN) and a wide area network (WAN), but may also include other networks such as a virtual private network (VPN), an office network, an enterprise network, an intranet, the Internet, etc. It will be appreciated that the network connections shown are exemplary and other means of establishing a communications link between the computers 900, 944 may be used.

As used herein, the computer 900 includes or is operable to execute appropriate custom-designed or conventional software to perform and implement the processing steps of the method and system of the present invention, thereby forming a specialized and particular computing system. Accordingly, the presently-invented method and system may include one or more computers 900 or similar computing devices having a computer-readable storage medium capable of storing computer-readable program code or instructions that causes the processing unit 904 to execute, configure, or otherwise implement the methods, processes, and transformational data manipulations discussed hereinafter in connection with the present invention. Still further, the computer 900 may be in the form of a personal computer, a personal digital assistant, a portable computer, a laptop, a palmtop, a mobile device, a mobile telephone, a server, or any other type of computing device having the necessary processing hardware to appropriately process data to effectively implement the presently-invented computer-implemented method and system.

It will be apparent to one skilled in the relevant art(s) that the system may utilize databases physically located on one or more computers which may or may not be the same as their respective servers. For example, programming software on computer 900 can control a database physically stored on a separate processor of the network or otherwise.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice of those skilled in the art to which this disclosure pertains and which fall within the limits of the appended claims.

The invention claimed is:

1. A system for targeting and verifying a medical procedure, comprising:
   at least one screen for displaying a visual representation of the medical procedure;

at least one interface device for receiving data from at least one user;

at least one processor in communication with the at least one screen and the at least one interface device; and at least one computer-readable medium in communication with the at least one processor, having stored thereon instructions that, when executed by the at least one processor, cause the at least one processor to:

determine, from at least one three-dimensional image of at least a portion of a patient's anatomy, location and orientation data of at least one anatomical reference point, at least one external reference point, and at least one target point;

generate, from at least a portion of the location and orientation data, a frame coordinate map and a customized patient reference map;

position a predetermined stereotactic frame coordinate map over the three-dimensional image such that the frame coordinate map is aligned with the at least one anatomical point;

rotate the frame coordinate map about the at least one anatomical point such that the frame coordinate map coincides with the customized patient reference map;

generate, from the coincident frame coordinate map and customized patient reference map, a customized digital model comprising the at least one target point, the at least one anatomical reference point, and at least one customized positioning interface device, the customized positioning device being unique to the patient;

display the customized digital model on at least one screen; and simulate a medical procedure on the customized digital model, wherein the simulation comprises displaying, on at least one screen, at least one trajectory of a medical device or medical treatment to the at least one target point.

2. The system of claim 1, wherein the instructions further cause the at least one processor to fabricate, from the customized digital model, at least one customized positioning interface device.

3. The system of claim 2, wherein the at least one customized positioning interface device is a fixation post.

4. The system of claim 1, wherein the step of simulating the medical procedure comprises allowing a user to input information.

5. The system of claim 1, wherein the step of simulating the medical procedure comprises superimposing or placing the customized digital model on or in the three-dimensional image.

6. The system of claim 1, wherein the instructions further cause the at least one processor to obtain the three-dimensional image.

7. The system of claim 6, wherein the three-dimensional image is provided by one of a CT scan, a T1-weighted MRI scan, a T2-weighted MRI scan, and a PET scan.

8. The system of claim 1, wherein the at least one external reference point is an anchor implanted in the patient's body.

9. The system of claim 8, wherein the anchor is a detectable emitter.

10. The system of claim 9, wherein the detectable emitter is an active emitter or a passive emitter.

11. The system of claim 1, wherein the at least one anatomical reference point is at least one of the anterior commissure, posterior commissure, and mid-commissural point.

12. The system of claim 1, wherein the customized digital model further comprises at least one surgical entry point.

13. The system of claim 1, wherein the customized digital model further comprises at least one stereotactic targeting device and at least one fiducial registration device.

* * * * *